(12) United States Patent
Chen et al.

(10) Patent No.: US 8,663,711 B2
(45) Date of Patent: Mar. 4, 2014

(54) USE OF ARMILLARIDIN FOR TREATING CANCER

(75) Inventors: Yu-Jen Chen, Taipei (TW); Chien-Chih Chen, Taipei (TW)

(73) Assignee: Mackay Memorial Hospital, New Taipei (TW)

( * ) Notice: Subject to any disclaimer, the term of this patent is extended or adjusted under 35 U.S.C. 154(b) by 1 day.

(21) Appl. No.: 13/342,642

(22) Filed: Jan. 3, 2012

(65) Prior Publication Data

US 2013/0172656 A1     Jul. 4, 2013

(51) Int. Cl.
    *A61K 36/00*     (2006.01)
    *A61K 38/00*     (2006.01)
    *A61N 5/00*     (2006.01)

(52) U.S. Cl.
    USPC .............................. 424/725; 514/19.3; 600/1

(58) Field of Classification Search
None
See application file for complete search history.

(56) References Cited

U.S. PATENT DOCUMENTS

2004/0253266 A1 *   12/2004   Cheung .................... 424/195.16
2011/0262561 A1     10/2011   Chen et al.

OTHER PUBLICATIONS

Bohnert et al, In vitro cytotoxicity of melleolide antibiotics: structural and mechanistic aspects. Bioorganic & medicinal chemistry letters, (Apr. 1, 2011) vol. 21, No. 7, pp. 2003-2006.*

* cited by examiner

*Primary Examiner* — Tuan H Nguyen
(74) *Attorney, Agent, or Firm* — Muncy, Geissler, Olds & Lowe, P.C.

(57) ABSTRACT

Novel Uses of an aromatic ester isolated from *Armillaria mellea*, particularly, armillaridin, are disclosed herein. The armillaridin is useful for manufacturing a medicament or a pharmaceutical composition for suppressing the growth of cancerous cells or for enhancing susceptibility of esophageal cancerous cells to a radiation treatment, in a subject.

11 Claims, 3 Drawing Sheets

USE OF ARMILLARIDIN FOR TREATING CANCER

BACKGROUND OF THE INVENTION

1. Field of the Invention

The present disclosure relates to novel use of a small molecule isolated from *Armillaria mellea*, particularly, the use of armillaridin for manufacturing a medicament or a pharmaceutical composition for treating esophageal cancer by enhancing its susceptibility to a radiation therapy.

2. Description of Related Art

Radiation therapy has been used to treat cancers and other diseases. However, the dose of effective radiation must be sufficiently limited to the tumor or other target tissue to avoid injuring the surrounding tissue and the overall health of the patient.

Some efforts have been adopted to enhance the susceptibility of the tumor cells toward radiation so that lower dose of radiation may be applied. For example, it has been shown that the presence of chemotherapeutic agents within the tumor during the treatment with a radiation therapy device can somewhat improve treatment response. However, research in this regard is limited.

Therefore, there exists in the related art a need of an agent or a compound that is useful for enhancing susceptibility of a cancer toward a radiation therapy, hence such agent or compound may be used as an adjuvant of anti-cancer drugs for treating cancer, particularly, esophageal cancer.

SUMMARY

The present disclosure is based, at least in part, unexpected discovery that a protoilludance norsesquilterpenoid ester compound isolated from *Armillaria mellea* possesses anti-proliferative activity toward cancerous cells, including human esophageal cancerous cells; as well as enhancing susceptibility of the esophageal cancerous cells to a radiation treatment. Therefore, this active compound alone is useful as a therapeutic agent, or as an adjuvant of other anti-cancer drugs, to suppress or retard the growth of esophageal cancer.

Accordingly, it is the first aspect of the present disclosure to provide a novel use of armillaridin for manufacturing a medicament or a pharmaceutical composition for enhancing susceptibility of esophageal cancerous cells to a radiation treatment. The medicament or the pharmaceutical composition comprises a therapeutically effective amount of armillaridin or a pharmaceutically acceptable salt thereof; and a pharmaceutically acceptable excipient.

Therefore, it is the second aspect of the present invention to provide a method of enhancing susceptibility of esophageal cancerous cells to a radiation therapy. The method includes the steps of, administering to the esophageal cancerous cells an effective amount of armillaridin or a pharmaceutically acceptable salt thereof; and subsequently applying a radiation therapy to the armillaridin-treated esophageal cancerous cells. The radiation therapy includes the step of irradiating the armillaridin-treated cancerous cells with a radiation source at an energy of 0.05 to 15 mega volts (MV), preferably 1 to 10 MV, and more preferably, 6 MV. In one example, the esophageal cancerous cells are squamous carcinoma cells. In another example, the esophageal cancerous cells are adenocarcinoma cells.

In further embodiments, the method may further comprise administering another agent that is known to improve the treatment of esophageal cancer before, together with and/or after administering armillaridin. Examples of *mellea* possesses anti-proliferative activity toward cancerous cells, including human esophageal cancerous cells; as well as enhancing susceptibility of the esophageal cancerous cells to a radiation treatment. Therefore, this active compound alone is useful as a therapeutic agent, or as an adjuvant of other anti-cancer drugs, to suppress or retard the growth of esophageal cancer.

Accordingly, it is the first aspect of the present disclosure to provide a novel use of armillaridin for manufacturing a medicament or a pharmaceutical composition for enhancing susceptibility of esophageal cancerous cells to a radiation treatment. The medicament or the pharmaceutical composition comprises a to therapeutically effective amount of armillaridin or a pharmaceutically acceptable salt thereof; and a pharmaceutically acceptable excipient.

Therefore, it is the second aspect of the present invention to provide a method of enhancing susceptibility of esophageal cancerous cells to a radiation therapy. The method includes the steps of, administering to the esophageal cancerous cells an effective amount of armillaridin or a pharmaceutically acceptable salt thereof; and subsequently applying a radiation therapy to the armillaridin-treated esophageal cancerous cells. The radiation therapy includes the step of irradiating the armillaridin-treated cancerous cells with a radiation source at an energy of 0.05 to 15 mega volts (MV), preferably 1 to 10 MV, and more preferably, 6 MV. In one example, the esophageal cancerous cells are squamous carcinoma cells. In another example, the esophageal cancerous cells are adenocarcinoma cells.

In further embodiments, the method may further comprise administering another agent that is known to improve the treatment of esophageal cancer before, together with and/or after administering armillaridin. Examples of such agent include, but are not limited to, alkylating agents, anthracyclines, plant alkaloids, topoisomerase inhibitors, cytotoxic antibiotics, tyrosine kinase inhibitors, and the like.

It is the third aspect of this disclosure to provide a method of treating esophageal cancer in a subject. The method includes the step of administering to the subject a therapeutically effective amount of armillaridin or a pharmaceutically acceptable salt thereof.

According to some embodiments of the present disclosure, armillaridin, when administered alone, is capable of arresting esophageal cancerous cells at $G_2/M$ phase.

In some embodiments, long-term exposure of armillaridin to the subject is effective in reducing the size of the cancer by at least 50%, as compared with that of the control, while exerting no adverse effects on the body weight or white blood cell counts of the subject. In these embodiments, armillaridin is repeatedly administered to the subject at a dose between 3-150 mg/Kg for at least 3-15 times during a time course of 3-30 days. In one specific example, the subject is given at least 12 doses of armillaridin at a dose of 80 mg/Kg within a period of 20 days, with 3 doses per week.

In further embodiments, the method further comprises administering to the subject another agent that is known to improve the treatment of cancer before, together with and/or after administering armillaridin. Examples of such agent include, but are not limited to, alkylating agents, anthracyclines, plant alkaloids, topoisomerase inhibitors, cytotoxic antibiotics and tyrosine kinase inhibitors, and the like.

It is therefore a fourth aspect of this invention to provide a novel use of armillaridin for manufacturing a medicament or a pharmaceutical composition for treating esophageal cancer. The medicament or the pharmaceutical composition comprises a therapeutically effective amount of armillaridin or a pharmaceutically acceptable salt thereof; and a pharmaceutically acceptable excipient.

The compound of this invention, armillaridin, is present at a level of about 0.1% to 99% by weight, based on the total weight of the pharmaceutical composition. In some embodiments, the compound of this invention is present at a level of at least 1% by weight, based on the total weight of the pharmaceutical composition. In certain embodiments, the compound of this invention is present at a level of at least 5% by weight, based on the total weight of the pharmaceutical composition. In still other embodiments, the compound of this invention is present at a level of at least 10% by weight, based on the total weight of the pharmaceutical composition. In still yet other embodiments, the compound of this invention is present at a level of at least 25% by weight, based on the total weight of the pharmaceutical composition.

The details of one or more embodiments of the invention are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The present description will be better understood from the following detailed description read in light of the accompanying drawings, wherein.

DETAILED DESCRIPTION OF PREFERRED EMBODIMENTS

Figure 1:
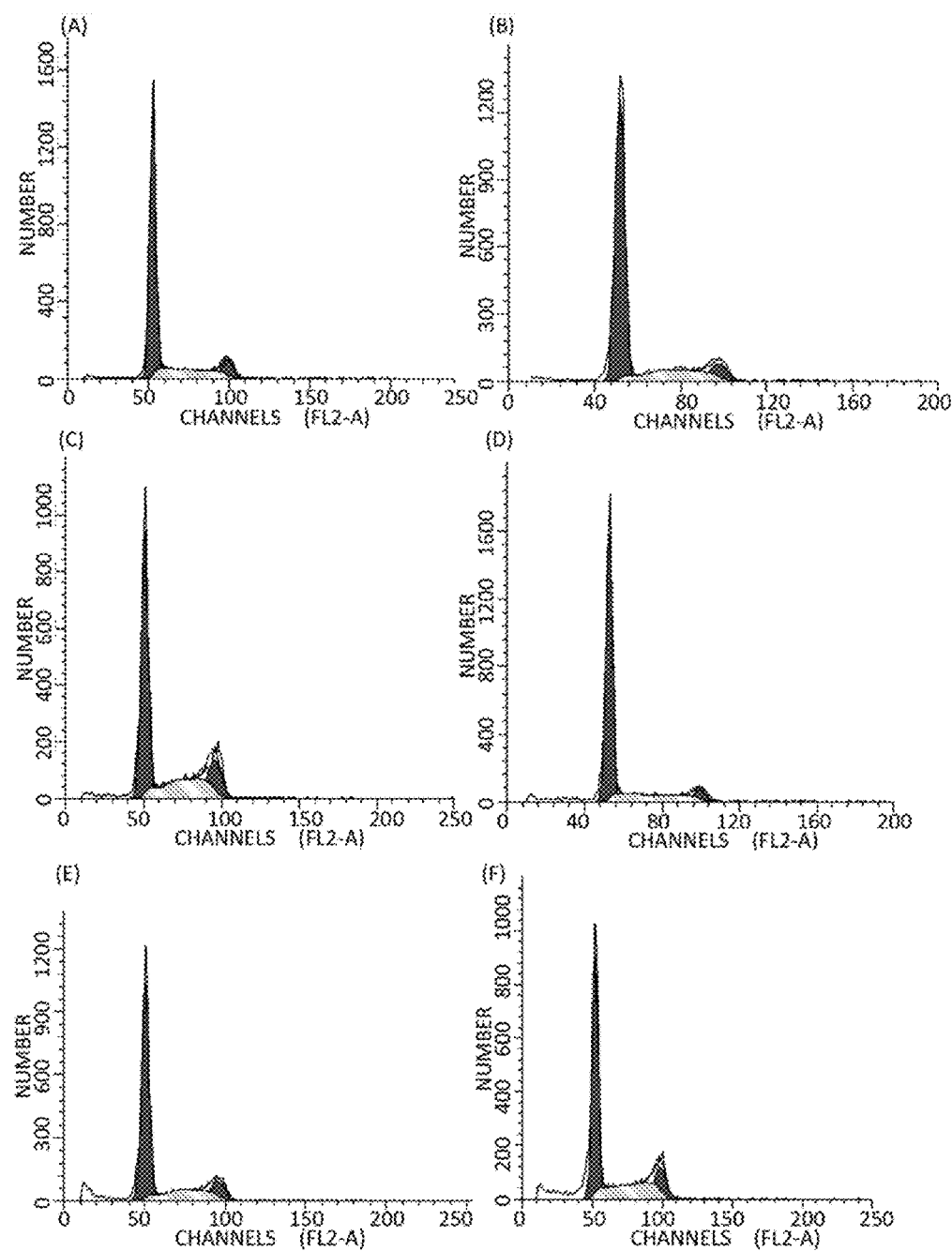
FIG. 1 illustrates the effects of CH-205-O (i.e., armillaridin) on cell cycle distribution in CE81T/VGH cells in accordance with one embodiment of this invention, in which upper panels represented results obtained from CE81T/VGH cells treated with 0 (panel A), 10 µM (panel B) or 20 µM (panel C) of CH-205-O for 48 hours, and lower panels represented results obtained from CE81T/VGH cells treated with 0 (panel D), 10 µM (panel E) or 20 µM (panel F) of CH-205-O for 72 hours.

The detailed description provided below in connection with the appended drawings is intended as a description of the present invention and is not intended to represent the only forms in which the present invention may be constructed or utilized.

In the context of this disclosure, a number of terms shall be used.

The term "treating" or "treatment" as used herein refers to administering a compound of this invention to arrest the growth of at least 45%, 50%, 55%, 60% or 65% of the cancerous cells at $G_2$/M cycle, preventing them from multiplying; and hence results in the reduction of the size of the cancer. Therefore, the term "treating" or "treatment" as used herein also refers to kill or induce apoptosis of the cancerous cells.

The term "an effective amount" as used herein refers to an amount effective, at dosages, and for periods of time necessary, to achieve the desired therapeutically desired result with respect to the treatment of cancer.

The terms "compound", "agent" or "medicament" are used interchangeably herein to refer to a compound or compounds or composition of which, when administered to a subject (e.g., a human or an animal) induces a desired pharmacological and/or physiological effect by local and/or systemic action.

The term "administered", "administering" or "administration" are used interchangeably herein to refer means either directly administering a compound or a composition of the present invention, or administering a prodrug, a derivative or an analog which will form an equivalent amount of the active compound within the body.

The term "subject" or "patient" refers to an animal including the human species that is treatable with the compound, compositions and/or methods of the present invention. The term "subject" or "patient" intended to refer to both the male and female gender unless one gender is specifically indicated. Accordingly, the term "subject" or "patient" comprises any mammal, preferably a human, which may benefit from treatment by the compound of this disclosure.

The present disclosure is based, at least in part, unexpected discovery that a protoilludance norsesquilterpenoid ester compound isolated from *Armillaria mellea* possess anti-proliferative activity toward cancerous cells, particularly, human esophageal cancerous cells, as well as enhancing susceptibility of the esophageal cancerous cells toward a radiation therapy. Therefore, this active compound alone is useful as a therapeutic agent, or as an adjuvant of other anti-cancer drugs to suppress or retard the growth of esophageal cancer cells.

*Armillaria mellea* (Tricholomataceae) is a medicinal fungus symbiotic with Chinese medicinal herb "Tianma" (*Gastrodia elata* Blume). The fruiting bodies of *Armillaria mellea* have been used in traditional Chinese medicine for the treatment of hypertension, headache, insomnia, dizziness, and vertigo. Previous chemical studies of the mycelium of *A. mellea* have identified a number of sesquiterpenoid aromatic esters having a protoilludane skeleton. Some of these sesquiterpenoids have been demonstrated to exhibit antimicrobial activities against gram-positive bacteria and yeast.

The active compound of the present disclosure isolated from *Armillaria mellea* is armillaridin or (2R,2aS,7bR)-3-formyl-2,2a,4a,5,6,7,7a,7b-octahydro-2a-hydroxy-6,6,7b-trimethyl-1H-cyclobuta[e]inden-2-yl 3-chloro-6-hydroxy-4-methoxy-2-methylbenzoate, and is termed "CH-205-O" hereafter. Shown below is the chemical structure of CH-205-O of this disclosure.

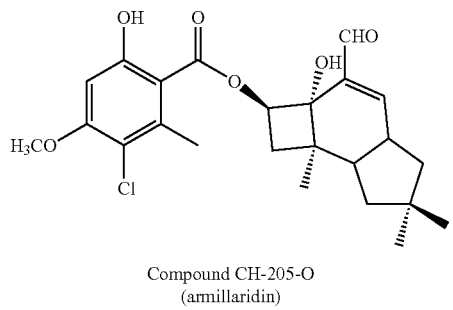

Compound CH-205-O
(armillaridin)

CH-205-O of this invention may be prepared in accordance with the process described in a co-pending U.S. patent application Ser. No. 13/093,080, entitled "Protoilludance Norsesquiterpenoid Esters and Uses Thereof" filed on Apr. 25, 2011, by Chen et el. The entire disclosure of which is herein incorporated by reference.

Accordingly, this disclosure provides a method of enhancing susceptibility of esophageal cancerous cells to a radiation therapy. The method includes the steps of, administering to the esophageal cancerous cells an effective amount of CH-205-O or a pharmaceutically acceptable salt thereof; and subsequently applying a radiation therapy to the CH-205-O-treated esophageal cancerous cells. The radiation therapy includes the step of irradiating the CH-205-O-treated cancerous cells with a radiation source emitting radiation at an energy of about 0.05 to 15 mega volts (MV), such as 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14 or 15 MV for a time and under conditions sufficient to kill cancerous cells within the target tissue. Preferably, the radiation source emits radiation at an energy of about 1 to 10 MV, such as 1, 2, 3, 4, 5, 6, 7, 8, 9, or 10 MV; and more preferably about 6 MV. In one example, the esophageal cancerous cells are squamous carcinoma cells. In another example, the esophageal cancerous cells are adenocarcinoma cells.

The method may further include steps of administering another agent that is known to improve the treatment of esophageal cancer before, together with and/or after administering CH-205-0. Examples of such agent include, but are not limited to, alkylating agents, anthracyclines, plant alkaloids, topoisomerase inhibitors, cytotoxic antibiotics and tyrosine kinase inhibitors, and the like.

Examples of alkylating agent include, but are not limited to, cisplatin, carboplatin, oxaliplatin, cyclophosphamide, chlorambucil, ifosfamide and the like. Examples of anthracyclines include, but are not limited to, doxorubicin, daunorubicin, valrubicin, idarubicin and the like. Examples of plant alkaloids include, but are not limited to, vincristine, vinblastine, taxol, docetaxel and the like. Examples of topoisomerase inhibitors include, but are not limited to, camptothecin (CPT), irinotecan (CPT-11), topotecan (TPT) and the like. Examples of cytotoxic antibiotics include, but are not limited to, antinomycin, bleomycin, mitomycin, plicamycin and the like. Examples of tyrosine kinase inhibitors include, but are not limited to, nilotinib, imatinib, gefitinib, erlotinib, cetuximab, panitumumab, zalutumumab, nimotuzumab, matuzuman and the like.

In addition to the method of enhancing susceptibility of cancerous cells to radiation treatment, the present disclosure also provides a method of treating cancer in a subject. The method includes administering to the subject an effective amount of CH-205-O described above or a pharmaceutically acceptable salt thereof. The CH-205-O of this disclosure, after being administering to the subject, is effective in suppressing the growth of cancerous cells. According to one embodiment of the present disclosure, the cancer that may be treated by CH-205-O is esophageal cancer, in which surgery removal of the esophageal cancerous tissue remains the primary means for its treatment. In one specific example, CH-205-O is effective in arresting at least 50% of the esophageal cancerous cells at $G_2$/M cycle, preventing them from multiplying.

In some embodiments, the effective amount of the compound of this invention administered to the subject is from about 1 to 150 mg/Kg body weight of the subject by oral ingestion, intravenous or intramuscular injection. The amount is administered to the subject at about 10, 20, 30, 40, 50, 60, 70, 80, 90, 100, 110, 120, 130, 140 or 150 mg/Kg body weight of the subject per day, preferably about 30 to 120 mg/Kg body weight of the subject, such as 30, 40, 50, 60, 70, 80, 90, 100, 110 Or 120 mg/Kg body weight of the subject per day; more preferably about 50 to 100 mg/Kg body weight of the subject per day, such as 50, 60, 70, 80, 90 or 100 mg/Kg body weight of the subject per day; most preferably about 80 mg/Kg body weight of the subject per day. These dose can be administered in a single dosage, or alternatively in more than one dosage.

According to one specific embodiment of the present disclosure, long-term exposure of CH-205-O to the subject is effective in reducing the size of the cancer by at least 50%, as compared with that of the control, while exerting no adverse effects on the body weight or white blood cell counts of the subject. Preferably, CH-205-O is repeatedly administered to the subject at a dose of 50 to 120 mg/Kg, such as 50, 60, 70, 80, 90, 100, 110, or 120 mg/Kg for at least 3 to 15 times, such as 3, 4, 5, 6, 7, 8, 9, 10, 11, 12, 13, 14 or 15 times during a time course of 3 to 30 days, such as 3, 4, 5, 6, 7, 8, 9, 10, 11, 12, 13, 14, 15, 16, 17, 18, 19, 20, 21, 22, 23, 24, 25, 26, 27, 28, 29 or 30 days. More preferably, CH-205-O is repeatedly administered to the subject at a dose of 70 to 100 mg/Kg, such as 70, 80, 90, or 100 mg/Kg for at least 5 to 10 times, such as 5, 6, 7, 8, 9, or 10 times during a time course of 7 to 25 days, such as 7, 8, 9, 10, 11, 12, 13, 14, 15, 16, 17, 18, 19, 20, 21, 22, 23, 24, or 25 days. The doses may be administered on a daily basis or 3 to 5 times per week, depends on the conditions and disease status of the patient. In one specific example, the subject is given at least 12 doses of CH-205-O within a period of 20 days, with 3 doses per week.

In some embodiments, the method further includes the step of administering another agent that is known to improve the treatment of cancer, before, together with and/or after administering the compound of this invention. Examples of such agent include, but are not limited to, alkylating agents, anthracyclines, plant alkaloids, topoisomerase inhibitors, cytotoxic antibiotics, tyrosine kinase inhibitors, and the like.

Examples of alkylating agent include, but are not limited to, cisplatin, carboplatin, oxaliplatin, cyclophosphamide, chlorambucil, ifosfamide and the like. Examples of anthracyclines include, but are not limited to, doxorubicin, daunorubicin, valrubicin, idarubicin and the like. Examples of plant alkaloids include, but are not limited to, vincristine, vinblastine, taxol, docetaxel and the like. Examples of topoisomerase inhibitors include, but are not limited to, camptothecin (CPT), irinotecan (CPT-11), topotecan (TPT) and the like. Examples of cytotoxic antibiotics include, but are not limited to, antinomycin, bleomycin, mitomycin, plicamycin and the like. Examples of tyrosine kinase inhibitors include, but are not limited to, nilotinib, imatinib, gefitinib, erlotinib, cetuximab, panitumumab, zalutumumab, nimotuzumab, matuzuman and the like.

This disclosure also provides a pharmaceutical composition for treating cancer; the composition comprises a therapeutically effective amount of the compound of this invention as shown above; and a pharmaceutically acceptable excipient.

Generally, the compound of this invention is present at a level of about 0.1% to 99% by weight, based on the total weight of the pharmaceutical composition. In some embodiments, the compound of this invention is present at a level of at least 1% by weight, based on the total weight of the pharmaceutical composition. In certain embodiments, the compound of this invention is present at a level of at least 5% by weight, based on the total weight of the pharmaceutical composition. In still other embodiments, the compound of this invention is present at a level of at least 10% by weight, based on the total weight of the pharmaceutical composition. In still yet other embodiments, the compound of this invention is present at a level of at least 25% by weight, based on the total weight of the pharmaceutical composition.

In some embodiments, the medicament of said pharmaceutical composition of this invention further includes an agent that is known to improve the treatment of cancer. Examples of such agent include, and are not limited to, alkylating agents, anthracyclines, plant alkaloids, topoisomerase inhibitors, cytotoxic antibiotics and tyrosine kinase inhibitors, and the like.

The medicament or said pharmaceutical composition is prepared in accordance with acceptable pharmaceutical procedures, such as described in Remington's Pharmaceutical Sciences, 17$^{th}$ edition, ed. Alfonoso R. Gennaro, Mack Publishing Company, Easton, Pa. (1985). Pharmaceutically acceptable excipients are those that are compatible with other ingredients in the formulation and biologically acceptable.

The compounds of this invention (i.e., CH-205-O) may be administered by any suitable route, for example, orally in capsules, suspensions or tablets or by parenterally administration. Parenterally administration can include, for example, systemic administration such as intramuscular, intravenous, subcutaneous, or intraperitoneal injection. The compound can also be administered transdermally either topically or by inhalation (e.g., intrabronichial, intranasal, oral inhalation or intranasal drops), or rectally, alone or in combination with conventional pharmaceutically acceptable excipients. In preferred embodiments, the compounds of this invention are administered orally (e.g., dietary) to the subject.

For oral administration, the compounds of the present invention may be formulated into tablets containing various excipients such as microcrystalline cellulose, sodium citrate, calcium carbonate, dicalcium phosphate, and glycine; along with various disintegrants such as starch, alginic acid and certain silicates; together with granulation binders like polyvinylpyrrolidone, sucrose, gelatin and acacia. Additionally, lubricating agents such as magnesium stearate, sodium lauryl sulfate and talc may be added. Solid composition may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and if so desired, emulsifying and/or suspending agents as well, together with diluents such as water, ethanol, propylene glycol, glycerin and a combination thereof.

For parenteral administration, the compounds of the present invention may be formulated into liquid pharmaceutical compositions, which are sterile solutions, or suspensions that can be administered by, for example, intravenous, intramuscular, subcutaneous, or intraperitoneal injection. Suitable diluents or solvent for manufacturing sterile injectable solution or suspension include, but are not limited to, 1,3-butanediol, mannitol, water, Ringer's solution, and isotonic sodium chloride solution. Fatty acids, such as oleic acid and its glyceride derivatives are also useful for preparing injectables, as are natural pharmaceutically-acceptable oils, such as olive oil or castor oil. These oil solutions or suspensions may also contain alcohol diluent or carboxymethyl cellulose or similar dispersing agents. Other commonly used surfactants such as Tweens or Spans or other similar emulsifying agents or bioavailability enhancers that are commonly used in manufacturing pharmaceutically acceptable dosage forms can also be used for the purpose of formulation.

For topical administration, the medicament or said pharmaceutical compositions of this invention may be formulated into a variety of dosage forms for topical application. A wide variety of dermatologically acceptable inert excipients well known to the art may be employed. The topical compositions may include liquids, creams, lotions, ointments, gels, sprays, aerosols, skin patches, and the like. Typical inert excipients may be, for example, water, ethyl alcohol, polyvinyl pyrrolidone, propylene glycol, mineral oil, stearyl alcohol and gel-producing substances. All of the above dosages forms and excipients are well known to the pharmaceutical art. The choice of the dosage form is not critical to the efficacy of the composition described herein.

For transmucosal administration, the medicament or said pharmaceutical compositions of this invention may also be formulated in a variety of dosage forms for mucosal application, such as buccal and/or sublingual drug dosage units for drug delivery through oral mucosal membranes. A wide variety of biodegradable polymeric excipients may be used that are pharmaceutically acceptable, provide both a suitable degree of adhesion and the desired drug release profile, and are compatible with the active agents to be administered and any other components that may be present in the buccal and/or sublingual drug dosage units. Generally, the polymeric excipient comprises hydrophilic polymers that adhere to the wet surface of the oral mucosa. Examples of polymeric excipients include, but are not limited to, acrylic acid polymers and copolymers; hydrolyzed polyvinylalcohol; polyethylene oxides; polyacrylates; vinyl polymers and copolymers; polyvinylpyrrolidone; dextran; guar gum; pectins; starches; and cellulosic polymers.

Accordingly, this invention also provides methods of treating mammals, preferably humans, for cancer, which comprises the administration of the medicament or said pharmaceutical composition of this invention that contains a compound of this invention. Such medicament or composition is administered to a mammal, preferably human, by any route that may effectively transports the active ingredient(s) of the composition to the appropriate or desired site of action, such as oral, nasal, pulmonary, transdermal, such as passive or iontophoretic delivery, or parenteral, e.g., rectal, depot, subcutaneous, intravenous, intramuscular, intranasal, ophthalmic solution or an ointment. Further, the administration of the compound of this invention with other active ingredients may be concurrent or simultaneous.

It will be appreciated that the dosage of compounds of the present invention will vary from patient to patient not only for the particular compound or composition selected, the route of administration, and the ability of the compound (alone or in combination with one or more drugs) to elicit a desired response in the patient, but also factors such as disease state or severity of the condition to be alleviated, age, sex, weight of the patient, the state of being of the patient, and the severity of the pathological condition being treated, concurrent medication or special diets then being followed by the patient, and other factors which those skilled in the art will recognize, with the appropriate dosage ultimately being at the discretion of the attendant physician. Dosage regimens may be adjusted to provide the improved therapeutic response. A therapeutically effective amount is also one in which any toxic or detrimental effects of the compound or composition are outweighed by the therapeutically beneficial effects. Preferably, the compounds or compositions of the present invention are administered at a dosage and for a time such that the number and/or severity of the symptoms are decreased.

The present invention will now be described more specifically with reference to the following embodiments, which are provided for the purpose of demonstration rather than limitation.

EXAMPLES

Materials and Methods

Cell and Culture

Cell lines used in the present disclosure include human esophageal squamous carcinoma cell lines CE81T/VGH and TE-2, and human esophageal adenocarcinoma cell lines BE-3 and SKGT-4. Each cell lines were cultured and maintained in Dulbecco's modified Eagle media (DMEM) supplemented with 10% fetal calf serum, 100 IU/ml penicillin, 100 µg/ml streptomycin, and 2 mM glutamine in 5% $CO_2$ at 37° C.

Trypan Blue Exclusion Test

The dye exclusion test is used to determine the number of viable cells present in a cell suspension. It is based on the principle that live cells possess intact cell membranes that exclude certain dyes, such as trypan blue, eosin, or propidium, whereas dead cells do not. In this test, the cells were first treated with a test compound (i.e., CH-205-O) for a certain period of time (e.g., 72 hours), then the cells were harvested and re-suspended in suitable buffer solution. The cell suspension was then mixed with trypan blue dye and then visually examined to determine whether cells had taken up or excluded the dye. A viable cell will have a clear cytoplasm, whereas a nonviable cell will have a blue cytoplasm. The concentration required to reduce viability by 50% ($IC_{50}$) after 72 hours was extrapolated from the dose-response curves by different concentrations of the test compound using a second-order polynomial regression model and analyzing with SigmaPlot Software (Systat Software Inc., San Jose, Calif.).

Cell Cycle Analysis

Cultured cells with or without pre-treatment of the compound of this invention (i.e., armillaridin at 10 or 20 µM for 48 or 72 hours) were harvested from the cultured media and fixed by incubating with 75% iced cold ethanol at 4° C. for at least over night. The fixed cells were then warmed up to room temperature and treated with RNAase A for about 30 min. Precipitated cells were collected by centrifugation and re-suspended in a buffer solution containing propidium iodine (20 µg/ml) before being subject to flow cytometry analysis, where cell numbers at respective cell cycles were determined.

Radiation Treatment and Clonogenic Assay

Approximately 100 variable tumor cells were respectively plated onto 35-mm six-well culture dishes and were allowed to grow in DMEM medium contained 10% FCS mixed with 0, 1.25, 2.5 or 5 µM of the test compound of this disclosure (i.e., CH-205-O), and the test compound-treated cells were continued culture for 24 hours. The test compound was then washed out, and cells were subject to radiation treatment. Specifically, 6 MeV electron beam energy was delivered by a linear accelerator (Clinac 1800, Varian Associates, Inc., Palo Alto, Calif., USA) with a rate of 2.4 Gy/min at various dose including 0, 0.5, 1, 2, 3 and 4 Gy in a single fraction. Full electron equilibrium was ensured for each fraction by a parallel plate PR-60C ionization chamber (CAPINTEL, Inc., Ramsey, N.Y., USA).

After radiation treatment, cells were returned to the culture for another 14 days; then were stained with 3% crystal violet and the numbers of colony (≥50 cells) were counted.

Xenograft Esophageal Cancer Mice Model

For primary esophageal cancer model, total of 9 Balb/c nude mice at the age of 6 weeks were randomly divided into 3 groups, with 3 mice in each group. To start the experiment, each mice were injected with $5 \times 10^5$ CE81T/VGH cells subcutaneously to generate esophageal cancer on day 0, and then returned to culture for another 21 days to allow tumor progression. To evaluate the efficacy of the test compound, mice in the test group were given 3 doses of the test compound (CH-205-O at 80 mg/Kg/dose; or cisplatin at 2.5 mg/Kg/dose) every week, and total of 12 doses were given during a period of 20 days after treatment started on day 22. Tumor sizes were measured using calipers. The body weight and the white blood cell counts of each mice were respectively recorded every day throughout the experiment. Tumor volume was calculated using the formula: volume=width$^2$×length×0.52.

Example 1

Armillaridin Inhibits the Growth of Esophageal Cancer Cells

The human esophageal cancer cell lines including squamous cell carcinoma cell lines CE81T/VGH and TE-2, and adenocarcinoma cell lines BE-3 and SKGT-4 were cultured and maintained by procedures described above in the "Materials and Methods" Section. Anti-proliferative activity of armillaridin (hereafter "CH-205-O") on each cell lines was assessed by cell viability and cell cycle analysis.

Table I gives the effect of CH-205-O on cell viability of human esophageal cancer cell lines assessed by trypan blue exclusion test. It is evident that CH-205-O is effective in reducing the cell number of each cell lines, with $IC_{50}$ being about 7 and 3 µM for squamous cell lines CE81T/VGH and TE-2, respectively; and about 5 µM for both adenocarcinoma cell lines BE-3 and SKGT-4.

TABLE 1

The $IC_{50}$ values of CH-205-O for four human esophageal cancer cell lines

| Cell lines | $IC_{50}$ |
|---|---|
| Squamous cell carcinoma | |
| CE81T/VGH | 6.9 µM |
| TE-2 | 3.4 µM |
| Adenocarcinoma | |
| BE-3 | 5.4 µM |
| SKGT-4 | 5.5 µM |

Cell cycle analysis further indicated that CH-205-O (at a concentration of 10 or 20 µM for 48 hours) is capable of arresting the CE81T/VGH cells at $G_2$/M phase in a dose-dependent manner; and may further induce an increase in the sub-G1 population of cells after treatment for 72 hours (FIG. 1).

Example 2

Armillaridin Enhances the Susceptibility of Human Esophageal Cancer Cells to Radiation Treatment In this example, effects of CH-205-O on the susceptibility of human cancer cell line CE81T/VGH to radiation were investigated.

Figure 2:
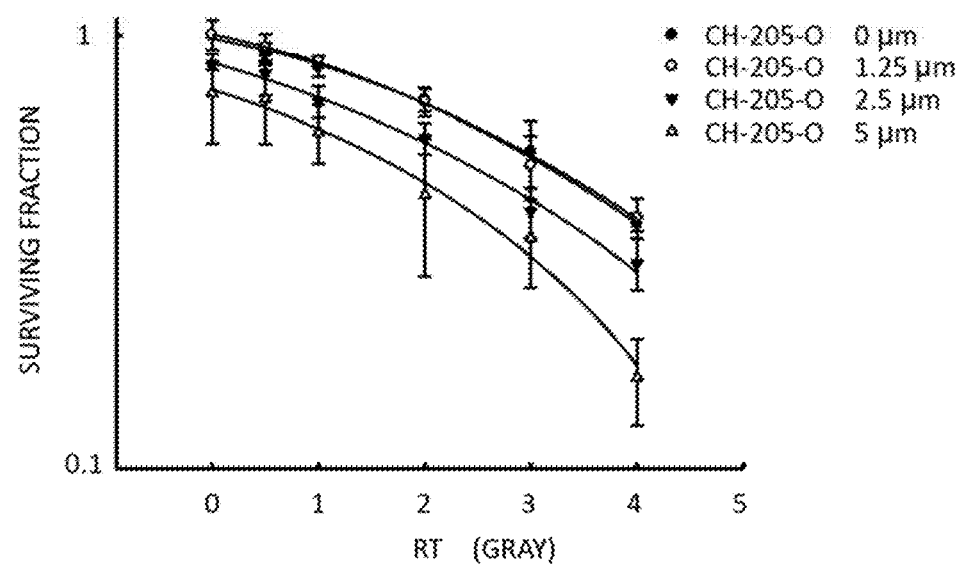
FIG. 2 illustrates the effects of CH-205-O on CE81T/VGH cells' susceptibility to radiation treatment in accordance with one embodiment of this invention.

To this purpose, cancerous cells were pre-treated with 1.25, 2.5 or 5 µM CH-205-O, before being treated with various doses of radiation in accordance with procedures described in "Materials and Methods" section. The survived cells were then subject to clonogenic assay, which is a test generally employed to determine the effect of drugs or radiation on the cells' ability to undergo unlimited division by counting the number of colony formed from a single cell. The colony is defined to consist of at least 50 cells. Results are illustrated in FIG. 2. CH-205-O, at dose of 2.5 or 5 μM, are capable of enhancing the susceptibility of CE81T/VGH cells to radiation treatment; hence armillaridin is a potential compound to act as an adjuvant for anti-cancer treatments.

Example 3

Figure 3:
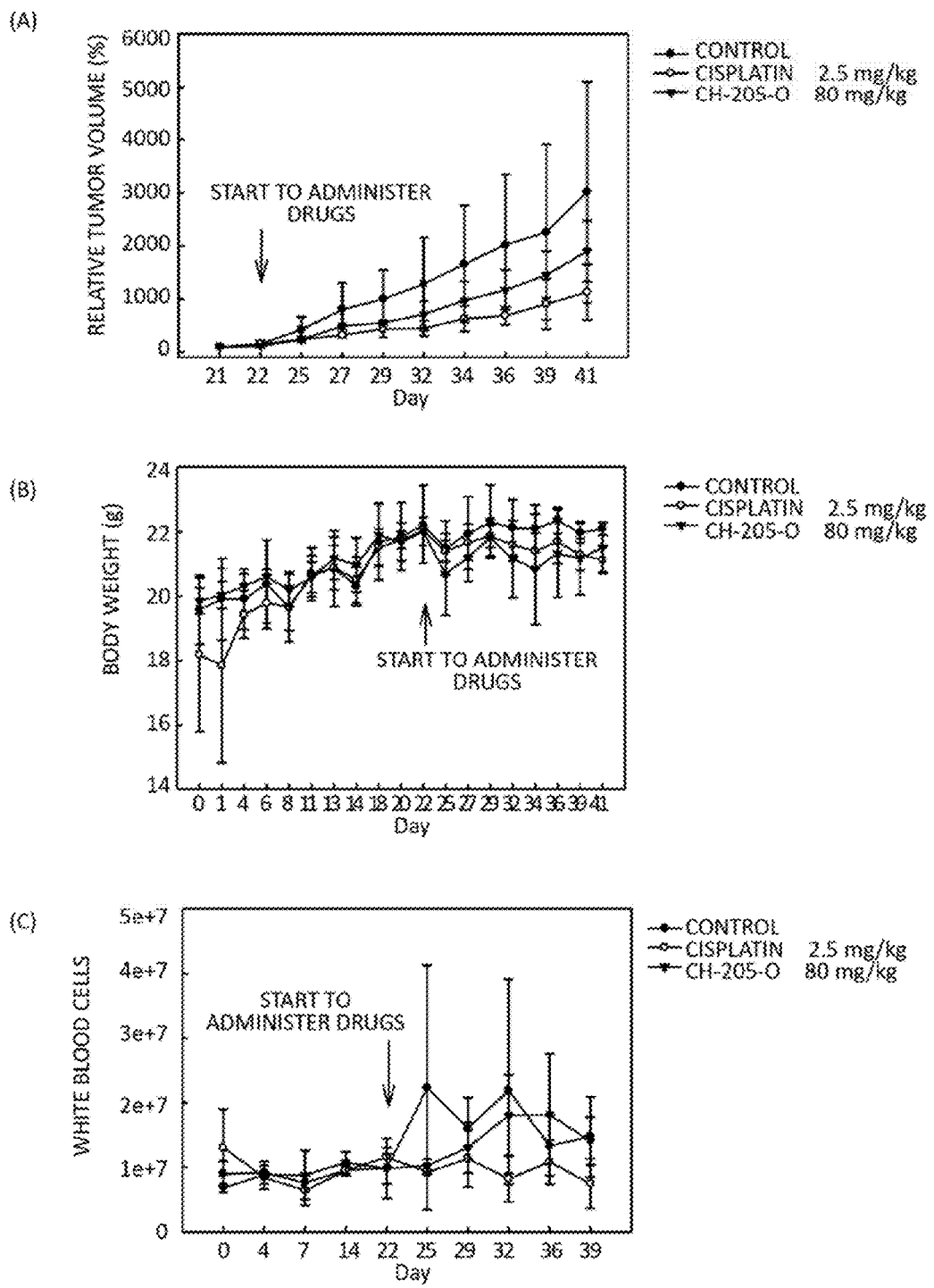
FIG. 3 illustrates the long-term exposure of CH-205-O on mice xenografted with CE81T/VGH cells in accordance with one embodiment of this invention.

Long-Term Armillaridin Treatment Inhibits the Growth of Human Esophageal Cancer Xenograft in Mice Effects of CH-205-O of this disclosure on mice grafted with CE81T/VGH cells were investigated by measuring the grafted tumor volume; body weight and the number of white blood cells of the mice in accordance with steps described in "Materials and Methods" section. Results are illustrated in FIG. 3.

As depicted in FIG. 3A, consecutively administrating CH-205-0, at the concentration of 80 mg/Kg/dose, for at least 12 doses, was effective in reducing the volume of the xenografted esophageal tumor significantly, as compared with that of the control mice (i.e., mice that were injected with vehicle only). At the same time, such long-term exposure with CH-205-O does not affect the body weight or the number of white blood cells of the mice (FIGS. 3B and 3C). Findings of this study indicate that CH-205-O is a potential compound for developing an anti-cancer medicament suitable for long-term usage.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of enhancing the susceptibility of esophageal cancer in a subject to a radiation therapy comprising administering to the subject an effective amount of armillaridin or a pharmaceutically acceptable salt thereof before irradiating the esophageal cancer with a radiation source at an energy of 1 to 10 mega volts.

2. The method of claim 1, wherein the radiation energy is 6 mega volts.

3. The method of claim 1, wherein the armillaridin or a pharmaceutically acceptable salt thereof is administered at a dose of 80 mg/Kg/day for at least 12 times.

4. The method of claim 1, further comprising administering to the subject an effective amount of a chemotherapy agent before, together with or after the administering of armillaridin.

5. The method of claim 4, wherein the chemotherapy agent is selected from the group consisting of an alkylating agent, an anthracycline, a plant alkaloid, a topoisomerase inhibitor, a cytotoxic antibiotic, and a tyrosine kinase inhibitor.

6. The method of claim 5, wherein the alkylating agent is cisplatin, carboplatin, oxaliplatin, cyclophosphamide, chlorambucil, or ifosfamide.

7. The method of claim 5, wherein the anthracycline is doxorubicin, daunorubicin, valrubicin, or idarubicin.

8. The method of claim 5, wherein the plant alkaloid is vincristine, vinblastine, taxol or docetaxel.

9. The method of claim 5, wherein the topoisomerase inhibitor is camptothecin (CPT), irinotecan (CPT-11) or topotecan (TPT).

10. The method of claim 5, wherein the cytotoxic antibiotic is antinomycin, bleomycin, mitomycin, or plicamycin.

11. The method of claim 5, wherein the tyrosine kinase inhibitor is imatinib, gefitinib, erlotinib, cetuximab, panitumumab, zalutumumab, nimotuzumab, or matuzumab.

* * * * *